United States Patent [19]

Takahashi et al.

[11] Patent Number: 5,002,056
[45] Date of Patent: Mar. 26, 1991

[54] NON-CONTACT TYPE TONOMETER

[75] Inventors: Susumu Takahashi; Fumio Ohtomo, both of Tokyo, Japan

[73] Assignee: Tokyo Kabushiki Kikai Kabushiki Kaisha, Japan

[21] Appl. No.: 313,299

[22] Filed: Feb. 21, 1989

Related U.S. Application Data

[63] Continuation of Ser. No. 743,417, Jun. 11, 1985, abandoned.

[30] Foreign Application Priority Data

Jun. 12, 1984 [JP] Japan .................................. 59-119099
Nov. 19, 1984 [JP] Japan .................................. 59-242279

[51] Int. Cl.$^5$ .............................................. A61B 3/16
[52] U.S. Cl. ..................................... 128/648; 128/652
[58] Field of Search ........................... 128/645–648, 128/652, 748; 73/78–79, 81

[56] References Cited

U.S. PATENT DOCUMENTS

| | | | |
|---|---|---|---|
| 3,538,754 | 11/1970 | Grolman et al. | 128/648 |
| 3,585,849 | 6/1971 | Grolman | 128/648 |
| 3,756,073 | 9/1973 | Lavallee et al. | 128/648 |
| 3,832,890 | 9/1974 | Grolman et al. | 128/648 |
| 3,882,718 | 5/1975 | Kriebel | 128/649 |
| 4,523,597 | 6/1985 | Sawa et al. | 128/652 |

FOREIGN PATENT DOCUMENTS 77153 8/1981 Romania.

OTHER PUBLICATIONS

"An Instrument for Self-Measurement of Intraocular Pressure", R. C. Zeimmer & J. T. Wilensky, IEEE Transactions on Biomedical Engineering, vol. BME-29, No. 3, pp. 178–183, Mar. 1982.

"A Non-Contact Applanation Tonometer", Forbes, et al., Archives of Ophthalmology, vol. 91, No. 2, pp. 134–140, Feb. 1974.

Primary Examiner—Kyle L. Howell
Assistant Examiner—J. P. Lacyk
Attorney, Agent, or Firm—Finnegan, Henderson, Farabow, Garrett & Dunner

[57] ABSTRACT

A non-contact type tonometer is disclosed. It has an arrangement for transfiguring a cornea to be tested by discharging a fluid to it. This first arrangement comprises a rotary solenoid, a cylinder, and a rotary solenoid driving circuit. It also has a second arrangement for detecting the physical quantity showing the transfiguration of the cornea. The second arrangement comprises a radiating optical system and a detecting optical system. It also has a circuit serving as a third arrangement for detecting the flow pressure of the fluid which has a correlation with an intraocular pressure. It has a fourth arrangement for establishing a correlation function curve between the physical quantity and the flow pressure of the fluid based on the information from the second and third arrangements, deducing a flow pressure value corresponding to the preset value of the physical quantity from the correlation function curve, and converting such deduced flow pressure value of the fluid to an intraocular pressure value.

14 Claims, 9 Drawing Sheets

NON-CONTACT TYPE TONOMETER

This application is a continuation of application Ser. No. 06/743,417, filed June 11, 1985 now abandoned.

BACKGROUND OF THE INVENTION

1. Field of the Invention

This invention relates to a tonometer, and more particularly to a non-contact type tonometer which measures intraocular pressure from a correlation between a measured flow pressure of a fluid for transfiguring a cornea of a patient's eye to be tested and a physical quantity showing the transfiguration of the cornea.

2. Description of the Related Art

Conventionally, a non-contact type tonometer is known as disclosed in, for example, U.S. Pat. No. 3,585,849. The related art disclosed in that patent includes a fluid pulse discharger for directing a fluid pulse which has a predetermined time-pressure functional relation against a corneal surface are of a patient's eye in order to transfigure the area from convexity, through applanation, to concavity, a light source to direct a light beam at the surface area, and a light detector to detect and indicate quantities of flux reflection of the light as a function of the time during which the corneal surface is transfigured from convexity, through applanation, to concavity. The related art tonometer measures an intraocular pressure of the patient's eye from the correlation between the time-pressure functional relation of the fluid pulse and the time between the directing of the fluid force against the corneal surface and the occurring of the first applanation of the cornea surface or the time between the first and second applanations.

The aforementioned non-contact type tonometer has the disadvantage that an indispensable condition for proper operation is the invariability of the time-pressure functional relation of the fluid pulse in every measurement. Therefore, if the time-pressure functional relation of the fluid pulse is different between measurements, a measurement error of the intraocular pressure will directly occur. Thus, the conventional non-contact type tonometer has the problem that the accuracy of measurement of the intraocular pressure is difficult to improve.

SUMMARY OF THE INVENTION

The present invention is accomplished in view of the problem inherent in the afore-mentioned related art.

It is therefore a general object of the present invention to provide a non-contact type tonometer wherein the measurement accuracy can be improved extensively.

The present invention is accomplished in view of a fact that there exists a direct correlation between the flow pressure of the fluid and the intraocular pressure. The constitutional feature of the present invention is that it comprises a fluid generator for discharging a fluid under pressure toward the cornea of a patient's eye to be tested in order to transfigure the cornea; a corneal transfiguration detector for opto-electrically detecting the transfiguration of the cornea; a pressure detector for detecting fluid pressure of the fluid generator at least at the time when the cornea is transfigured by a predetermined quantity; and intraocular pressure deducing means for deducing an intraocular pressure of the eye from the detected fluid pressure. The present invention also comprises fluid discharging means for discharging a fluid to a cornea to be tested in order to transfigure the cornea; corneal transfiguration detecting means for opto-electrically detecting the physical quantity showing the transfiguration of the cornea to be tested; flow pressure detecting means for detecting the flow pressure of the fluid which has a correlation with the intraocular pressure; and intraocular pressure value converting means for establishing a correlation function curve between the physical quantity showing the transfiguration of the cornea to be tested and the flow pressure based on information from the corneal transfiguration detecting means and the flow pressure detecting means, for deducing a value of the flow pressure corresponding to a predetermined value of the physical quantity from the correlation function curve, and for converting the deduced value of the flow pressure to the intraocular pressure value.

The tonometer of the present invention eliminates the measuring error attributable to the timewise measurement method that measures the intraocular pressure by using time as a parameter. Accordingly, the accuracy of the intraocular pressure measurement can be improved.

Also, according to the related art, it is an essential condition that the time-pressure functional relation not vary as between measurements. Therefore, if the time-pressure functional relation varies between measurements, measuring errors are likely to take place. Accordingly, the design, manufacture, and quality of the fluid discharge means in the related art device must be very precise. In the present invention, variations in the design, manufacture and quality of the fluid discharge means do not directly affect the measuring accuracy of the intraocular pressure. Accordingly, the design of the fluid discharge means, as well as its manufacture and quality control are simplified. Furthermore, even if a change of the time-pressure functional relation should occur due to a change in the density of the fluid as a result of temperature changes, there will be no adverse effect, since the present invention measures the corresponding pressure directly. In the transfiguring process of the present invention, a function curve is obtained to correlate the flow pressure value and the corneal transfiguration quantity. The intraocular pressure value is determined based thereon, in a manner whereby the accuracy can be improved extensively compared with the related art.

BRIEF DESCRIPTION OF THE DRAWINGS

The nature of this invention, as well as the manner in which the objects and advantages hereof are obtained, will be readily apparent from consideration of the following description with reference to the accompanying drawings, in which like reference characters denote the same or similar parts throughout the figures thereof and wherein.

DETAILED DESCRIPTION OF THE EMBODIMENTS

Figure 1:
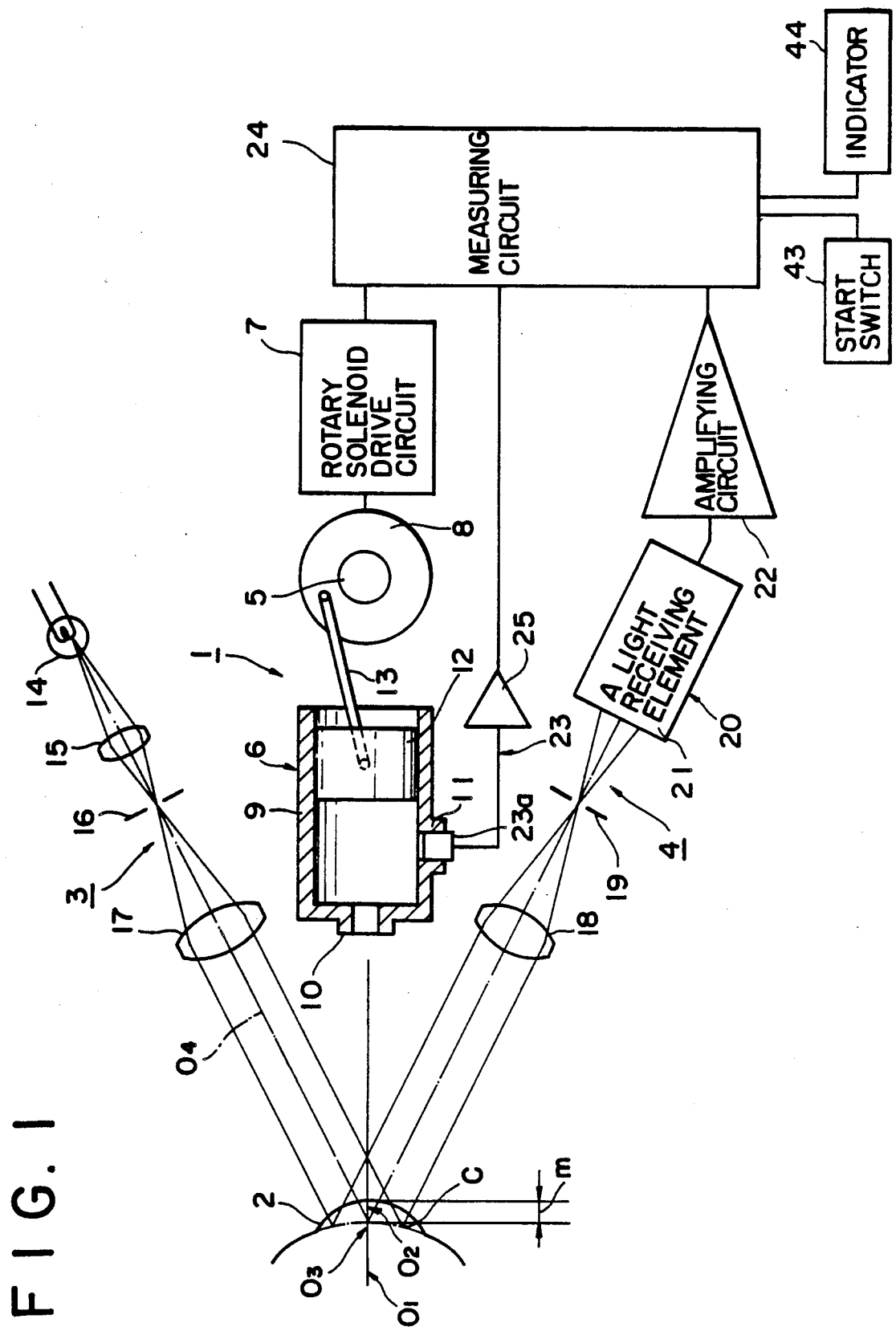
FIG. 1 is an overall constitutional view showing a first embodiment of a non-contact type tonometer according to the present invention.

FIG. 1 illustrates a first embodiment of a non-contact type tonometer according to the present invention. In FIG. 1, a fluid discharge means 1 is shown relative to a cornea 2 under test, a radiating optical system 3, and a detection optical system 4. The fluid discharge means 1 is adapted to discharge a fluid to the cornea 2 under test (hereinafter referred to as the "cornea") in order to transfigure the cornea 2. The fluid discharge means 1 generally comprises a rotary solenoid 5, a cylinder 6, and a rotary solenoid drive circuit 7. A drum 8 is mounted on the rotary solenoid 5.

The cylinder 6 includes a hollow cylindrical portion 9 and a hollow nozzle portion 10. The hollow cylindrical portion 9 is provided with a piston 12 for reciprocal movement. The piston 12 is connected to the drum 8 of the rotary solenoid 5 through a piston rod 13. The hollow nozzle portion 10 extends straight toward the cornea 2, and the fluid is discharged through the hollow nozzle portion 10 due to the reciprocal movement of the piston 12. On and off conditions of the rotary solenoid drive circuit 7 will be described hereinafter.

A flow pressure sensor 23a is inserted and secured within a sensor tube 11 extending from a side wall of the hollow cylindrical portion 9.

The cornea 2 is transfigured due to the flow of the pressurized fluid. According to the increase of the flow pressure, the cornea 2 is transfigured from convexity, through applanation, to concavity. Character C denotes the transfigured state of the cornea 2. Character m denotes its transfiguration quantity. If the vertex of the cornea 2 existing on the center line $O_1$ of the cornea 2 before transfiguration is designated at $O_2$ and the vertex of the cornea C existing on the center line $O_1$ of the cornea 2 after transfiguration is designated at $O_3$, the transfiguration quantity m denotes the distance between the vertexes $O_2$ and $O_3$.

The radiation optical system 3 and the detection optical system 4 constitute physical quantity detecting means or a cornea monitoring system for photoelectrically detecting the transfiguration quantity m of the cornea 2. The radiation optical system 3 comprises a light source 14, a condenser lens 15, a diaphragm 16 and a projecting lens 17. $O_4$ denotes an optical axis of the radiation optical system 3. The diaphragm 16 is positioned at the focal point of the projecting lens 17 between the condenser lens 15 and the projecting lens 17.

After being condensed by the condenser lens 15, the radiating light of the light source 14 becomes a detecting light formed of parallel pencil rays and is projected to the cornea 2. The detection optical system 4 comprises an image-formation lens 18, a diaphragm 19 and a photoelectric converter 20. The photoelectric converter 20 comprises a light receiving element 21 and an amplifying circuit 22. The light radiated from the radiation optical system 3 for passing through the cornea 2 is reflected and received by the light receiving element 21 through the image-forming lens 18 and the diaphragm 19, and photoelectrically converted. The corresponding electrical signals are outputted, through the amplifying circuit 22, as a detected light quantity corresponding to the transfiguration quantity m of the cornea 2.

A flow pressure detecting circuit 23 operates serving as flow pressure detecting means. The flow pressure detecting means 23 comprises the flow pressure sensor 23a and an amplifying circuit 25. This sensor 23a detects a flow pressure of a fluid which flows into the sensor tube 11 and corresponds to the pressure of the fluid being guided through, and discharged from, the hollow nozzle portion 10 to the cornea 2. A detected signal is outputted from the sensor 23a as a flow pressure detection signal through the amplifying circuit 25 to a measuring circuit 24.

The measuring circuit 24 serves as an intraocular pressure value converting means. The measuring circuit 24 functions to establish a correlation function curve between the detected light quantity corresponding to the transfiguration quantity m of the cornea 2 and the flow pressure detection signals to deduce from the correlation function curve the values of flow pressure corresponding to predetermined values of the transfiguration quantity m of the cornea 2. The measuring circuit 24 also converts such deduced values of flow pressure to values of the intraocular pressure.

Figure 2:
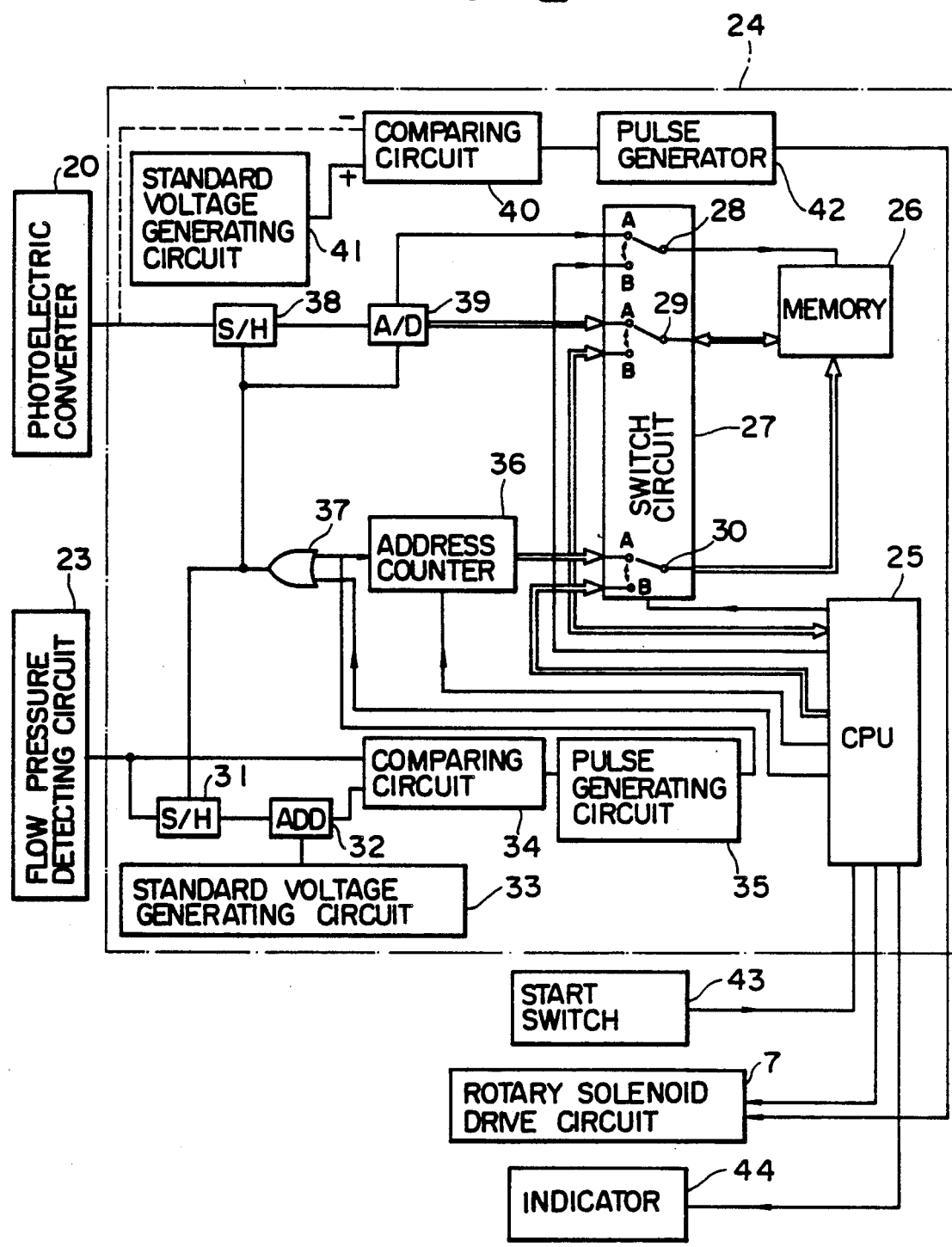
FIG. 2 is a block diagram of a measurement circuit for an intraocular pressure converting means of the non-contact type tonometer of FIG. 1.

As shown in FIG. 2, the measuring circuit 24 includes a central processing unit 25 (hereinafter referred to as a "CPU"), a memory circuit 26, and a switch circuit 27. The function of the CPU 25 will be described in relation with constitutional elements of other circuits.

In FIG. 2, the switch circuit 27 is shown as if it were a switch having contacts only for the convenience of explanation. In the figure, the switch circuit 27 includes three switches 28, 29 and 30. The switches 28, 29 and 30, respectively, include two switching contacts A and B. In addition, the measuring circuit 24 includes two sampling circuit systems for sampling data in order to establish the correlation function curve. One of the sampling circuit systems comprises a sample and hold circuit 31, an adding circuit 32, a standard voltage generating circuit 33, a comparing circuit 34, a pulse generating circuit 35, an address counter circuit 36, and an OR circuit 37.

The sample and hold circuit 31 is inputted with the flow pressure detection signals from the flow pressure detecting circuit 23, and includes a control terminal. When the control terminal is inputted with pulse signals, it performs sampling of the voltage of the flow pressure detection signals at that time and holds the voltage until pulse signals are next inputted in the control terminal. The adding circuit 32 adds the voltage values outputted from the sample and hold circuit 31 and voltage values generated by a standard voltage generating circuit 33, and outputs the sums of the voltage values.

The comparing circuit 34 receives at its plus terminal the output voltage of the adding circuit 32, and at its minus terminal the flow pressure detection signals. When the voltage of the flow pressure detection signal becomes larger than the output voltage of the adding circuit 32, the output of the comparing circuit 34 becomes a high level signal. When the output of the comparing circuit 34 becomes a high level signal, a single pulse signal is outputted from the pulse generating circuit 35. The pulse generating circuit 35 comprises, for example, a monostable multivibrator.

An address counter circuit 36 counts the pulse signals of the pulse generating circuit 35, and transmits the address information serving as its count value to the memory circuit 26 through the switch 30. The pulse signals of the pulse generating circuit 35 are also supplied to the control terminal of the sample and hold circuit 31 through the OR circuit 37. The OR circuit 37 also receives pulse signals from the CPU 25. That is, the sampling circuit system incrementally increases the address of the address counter circuit 36 at each step having a predetermined unitary pressure under the situation of increasing flow pressure of the fluid and corresponds its output to the address of the corresponding flow pressure data to obtain the address information.

The other sampling circuit system comprises a sample and hold circuit 38 and an analog-digital conversion circuit 39. The sample and hold circuit 38 is inputted with a detected light signal of the corneal reflecting optical quantity corresponding to the transfiguration quantity of the cornea 2 from the photoelectric converter 20 and includes a control terminal.

When the pulse signal outputted from the OR circuit 37 is received at the control terminal, the voltage value of the detected light signal at that time is sampled. This sampled voltage value is held until the next pulse signal is received by the control terminal.

The voltage value held by the sample and hold circuit 38 is converted to a digital quantity by the analog-digital conversion circuit 39 and supplied to the memory circuit 26 through the switch 29. Accordingly, in this sampling circuit system, at the same time when flow pressure data is sampled, a reflection optical quantity data corresponding to the corneal transfiguration quantity which corresponds to its flow pressure is sampled.

The measuring circuit 24 includes a circuit system for stopping the rotary solenoid 5. This circuit system comprises a comparing circuit 40, a standard voltage generating circuit 41, and a pulse generator 42. The comparing circuit 40 receives at its plus terminal the output voltage from the standard voltage generating circuit 41, and at its minus terminal the detected light signal from the photoelectric converter 20. The output voltage of the standard voltage generating circuit 41 is set at the voltage level of the detected light signal from the photoelectric converter 20, shortly before the time when the transfiguration quantity m of the cornea 2 becomes maximum. When the voltage of the detected light signal becomes higher than the output voltage of the standard voltage generating circuit 41, the comparing circuit 40 outputs a high level signal. When the output of the comparing circuit 40 changes to the high level signal from the low level signal, a single pulse signal is outputted from the pulse generating circuit 42. This pulse signal is inputted in the rotary solenoid drive circuit 7. When the rotary solenoid drive circuit 7 receives this pulse signal, it causes the rotary solenoid 5 to be stopped.

The CPU 25 is connected with a power switch (not shown), a start switch 43 and an indicator 44. When the power switch is turned on, a switch control signal is outputted to the switch circuit 27 from the CPU 25. As a result, the switches 28, 29, 30 are set at the B contact side to initialize the memory circuit 26. At the same time, a reset signal is supplied to the address counter 36 from the CPU 25, and the address counter 36 remains in its reset state. Thereafter, a switch control signal is again outputted to the switch circuit 27 from the CPU 25, and the switches 28, 29, 30 are set at the A contact side.

In this state, when the CPU 25 is switched on with a start switch 43 turned on, the CPU 25 carries out the following processing. First, the pulse signal is outputted to the OR circuit 37, and then the sample and hold circuits 31, 38 are made to carry out sampling of the voltage of the flow pressure detection signal as well as the voltage of the detected light signal corresponding to the cornea reflection optical quantity.

Simultaneously, the flow pressure data at this time and the optical quantity data are stored in the memory circuit 26. Since the fluid is not discharged and the cornea 2 is not yet transfigured, the voltage level of both the flow pressure detection signal and the detected light signal corresponding to the cornea reflection optical quantity is zero volts.

The comparing circuit 34 is supplied at its minus terminal with zero volts and at its plus terminal with the output voltage of the standard voltage generating circuit 33. Because of the foregoing, the output of the comparing circuit 34 is in its low level. Also, the output of the sample and hold circuit 38 is zero volts. The reset of the address counter 36 is canceled and thereafter, a drive control signal is inputted to the rotary solenoid driving circuit 7 to activate the rotary solenoid 5.

After the rotary solenoid 5 is activated, the cornea reflection optical quantity data corresponding to the cornea transfiguration quantity with respect to the flow pressure data obtained at each step of a predetermined unitary flow pressure is sampled by the two sampling circuit systems. Each sampled optical quantity data is stored in the memory circuit 26 at an address generated by the address counter 36.

In this process, when the output of the comparing circuit 40 changes to a low level from a high level, the rotary solenoid 5 is stopped, and the flow pressure of the fluid ceases increasing. Simultaneously, since the increasing of the voltage of the flow pressure detection signal is stopped and the output of the comparing circuit 34 is held in its low level thereafter and further sampling of the data is not carried out.

Figure 3:
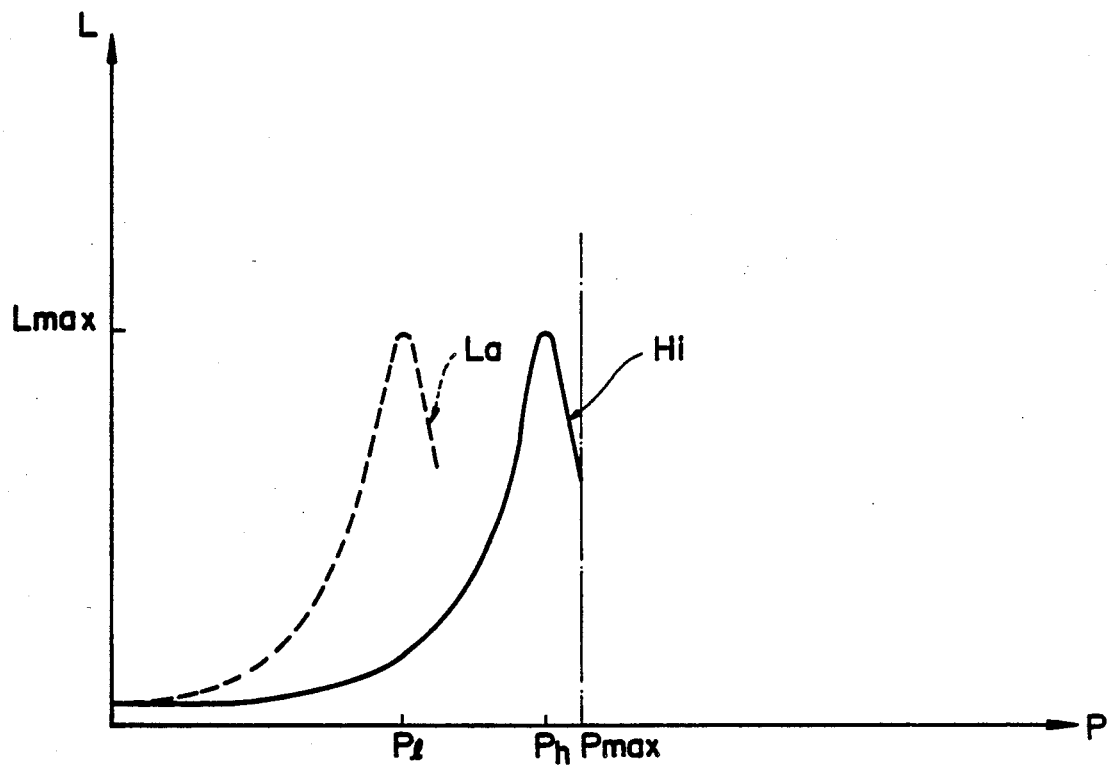
FIG. 3 is a graph of a correlation function established by the measurement circuit of FIG. 2.

After a predetermined time period set by a timer (not shown) of the CPU 25 has passed, a switch control signal is inputted toward the switch circuit 27 from the CPU 25, and the switches 28, 29, 30 are again set at the B contact side. The CPU 25 reads the sampling data stored in the memory circuit 26 and establishes a correlation function between the flow pressure data P as shown in FIG. 3 and the optical quantity L of the detected light corresponding to the corneal transfiguration quantity m based on the sampling data. In FIG. 3, Pmax denotes the maximum value of the flow pressure and the Lmax denotes the maximum value of the optical quantity. After establishing the correlation function, the CPU 25 deduces a flow pressure corresponding to the optical quantity which corresponds to the preset corneal transfiguration quantity from the correlation function and the deduced value is converted to an intraocular pressure value.

In this embodiment, for example, the flow pressure values $P_h$, $P_l$ at the maximum value Lmax of the optical quantity L are converted to intraocular pressure values. In FIG. 3, a curve Hi is shown by a solid line and a curve Lo is shown by a broken line. The lines Hi, Lo are for different corneas, respectively. Of course, needless to say, the cornea for the curve Hi is higher in its intraocular pressure value than the cornea for the other curve Lo. The intraocular pressure value obtained by the CPU 25 is indicated on the indicator 44.

Figure 4:
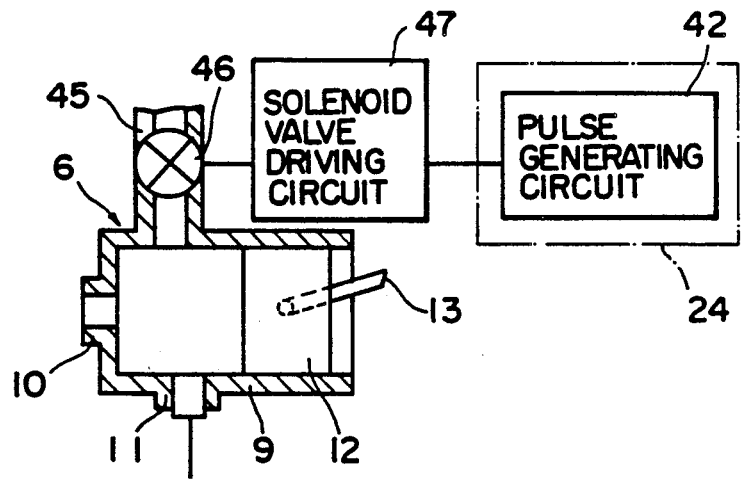
FIG. 4 is a constitutional view showing an example in which the fluid discharging means of FIG. 1 is modified.

As shown in FIG. 4, the cylinder 6 in this embodiment may be provided with a fluid escape cylindrical portion 45, which is provided with a solenoid valve 46 and a solenoid valve driving circuit 47 adapted to open the solenoid valve 46 upon receipt of the pulse signal of the pulse generating circuit 42 so that the flow pressure applied to the cornea 2 will be quickly decreased. Alternatively, a decrease of the flow pressure can be made quickly in the following manner. That is, when the rotary solenoid driving circuit 7 receives a pulse signal from the pulse generating circuit 42, the rotary solenoid 5 is actuated by the rotary solenoid driving circuit 7 in order to move the piston 12 backward when the piston 12 is in its progressing process.

Figure 5:
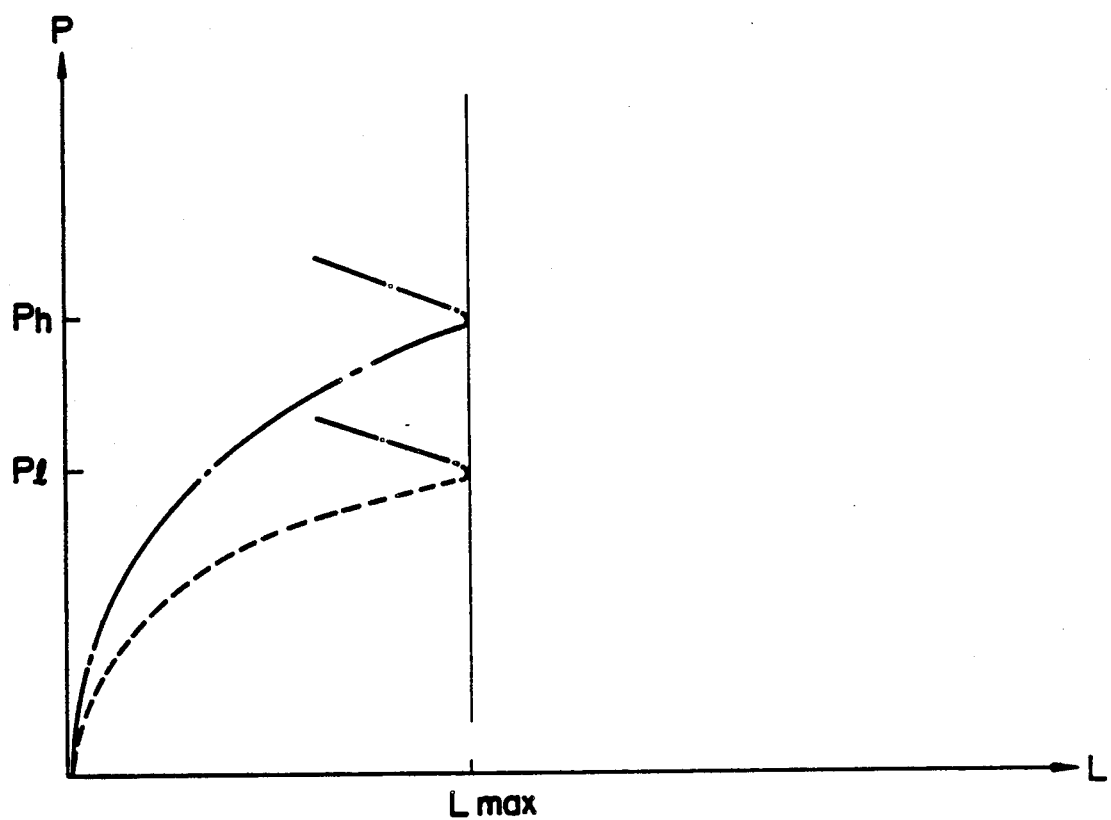
FIG. 5 is a graph of a correlation function in which the measurement circuit of FIG. 2 is modified.

Alternatively, the same purpose can be achieved by interchanging the photoelectric converter 20 and the flow pressure detecting circuit 23. In this case, the photoelectric converter 20 is connected to a circuit system at the side of the sample and hold circuit 31 and the flow pressure detecting circuit 23 is connected to a circuit system at the side of the sample and hold circuit 38. In this case, a correlation function is established as shown in FIG. 5.

A second embodiment of the non-contact type tonometer according to the present invention will be described with reference to FIG. 6. Since the tonometer in this second embodiment includes components similar to or identical with those in the first embodiment, identical reference numerals as used in the first embodiment are used for the corresponding components in the second embodiment.

Figure 6:
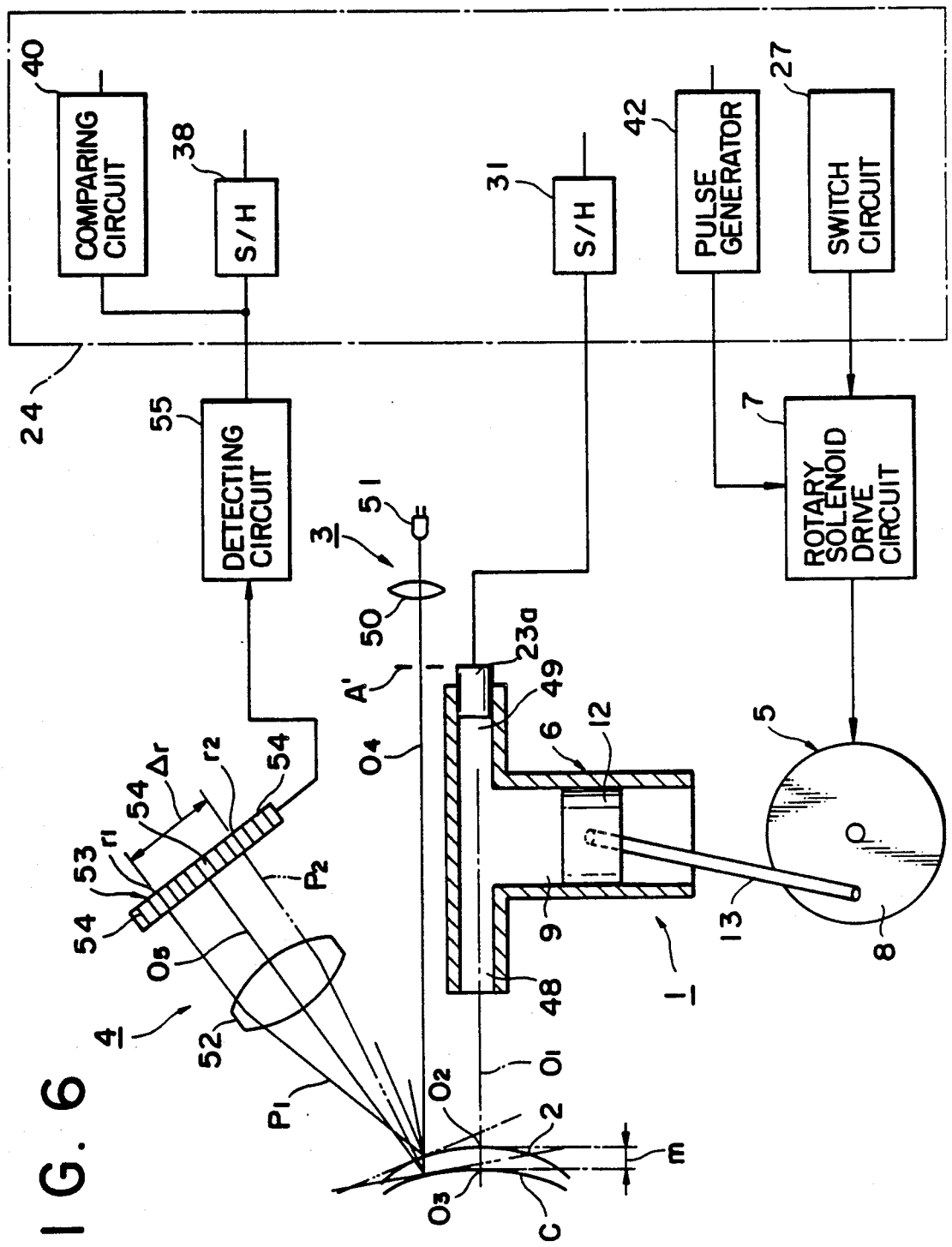
FIG. 6 is a schematic illustration of a second embodiment of the present invention.

In FIG. 6, a cylinder 6 of a fluid discharge means 1 is formed in the shape of the letter "T". This cylinder 6 includes the cylinder portion 9, and hollow nozzle portions 48 and 49. The hollow nozzle portion 48 extends straight toward the cornea 2. The hollow nozzle portion 49 extends straight in the opposite direction from the nozzle 48. The nozzle 49 is provided with a pressure sensor 23a in a tip portion thereof.

A fluid, e.g., air, under pressure generated by the reciprocal movement of the piston 12 in the cylinder 6 flows into the nozzles 48 and 49 and is discharged from the nozzle 48 toward the cornea 2.

A radiating optical system 3 includes a projecting lens 50 and an infrared emission diode 51. The projecting lens is disposed in a manner so that the optical axis $O_4$ of the projecting lens 50 is parallel with the axis $O_1$ of the cornea 2. The infrared emission diode 51 is disposed in such a manner that its emission center is positioned at a focal point of the projecting lens 50.

The projecting lens 50 is adapted to project toward the cornea 2 a spot light formed of parallel pencil rays serving as a detecting light through a diaphragm A'. A detecting optical system 4 includes an image-formation lens 52 and a photoelectric converter 53. The detecting optical system 4 receives the detecting light radiated from the radiating optical system 3 to allow it to pass through the cornea 2 and to photoelectrically convert its detected light for outputting a cornea transfiguration signal corresponding to the transfiguration quantity of the cornea. The image-formation lens 52 is disposed with its optical axis $O_5$ intersecting an optical axis $O_4$ at a point on the cornea when it is not transfigured by the fluid and has its normal convexity. The photoelectric converter 53 is provided at the focal point of the image formation lens 52 so that the detecting light reflected from the cornea 2 is received by the photoelectric converter 53. In this embodiment, a one dimension CCD linear sensor array is used for the photoelectric converter 53.

In FIG. 6, $P_1$ denotes a detecting light reflected on the cornea 2 prior to transfiguration and $P_2$ denotes a detecting light reflected on the cornea C after transfiguration by a quantity m. The detecting light $P_1$ is image-formed on the element $r_1$ of the component elements 54 of the photoelectric converter 53. The detecting light $P_2$ is image-formed on the element $r_2$ of the component elements 54.

The output signals from the photoelectric converter 53 are supplied to a detecting circuit 55. The detecting circuit 55 includes a sensor driver for producing the address information of a component element which is energized by the detected light as a digital signal. A digital to analog converter converts the digital signal outputted by the sensor driver to an analog signal in the form of a voltage.

The detecting circuit 55 outputs a voltage corresponding to the address information of the respective component elements 54. In the arrangement, the output of the detecting circuit 55 is supplied to the sample and hold circuit 38 and the comparing circuit 40 of the measuring circuit 24.

When the cornea 2 is transfigured by the quantity m, the image-formation position of the detecting light is changed by $\Delta r$. The magnitude of $\Delta r$, i.e., the change in the image-formation position, corresponds to the transfiguration quantity m. The change $\Delta r$ of the image-formation position is defined as a voltage difference.

The corneal transfiguration quantity data is sampled based on the output voltage of the detecting circuit 55.

Although a minute spot light is used for the radiating optical system in this embodiment, it may be formed in a circular pattern or a check-striped pattern projected on the cornea with its transfiguration quantity being detected.

Although a one-dimensional change of the image-formation position is used for the detecting optical system in this embodiment, a two-dimensional array may be used to detect the dimensional change of a circular pattern.

Furthermore, in the case that the person under test suffers from corneal astigmatism, since the position of the reflection spot, the displacement quantity will vary along the longitudinal direction of the cornea. In this case, the transfiguration detecting optical system may be arranged at, for example, every 60 degrees.

Figure 7:
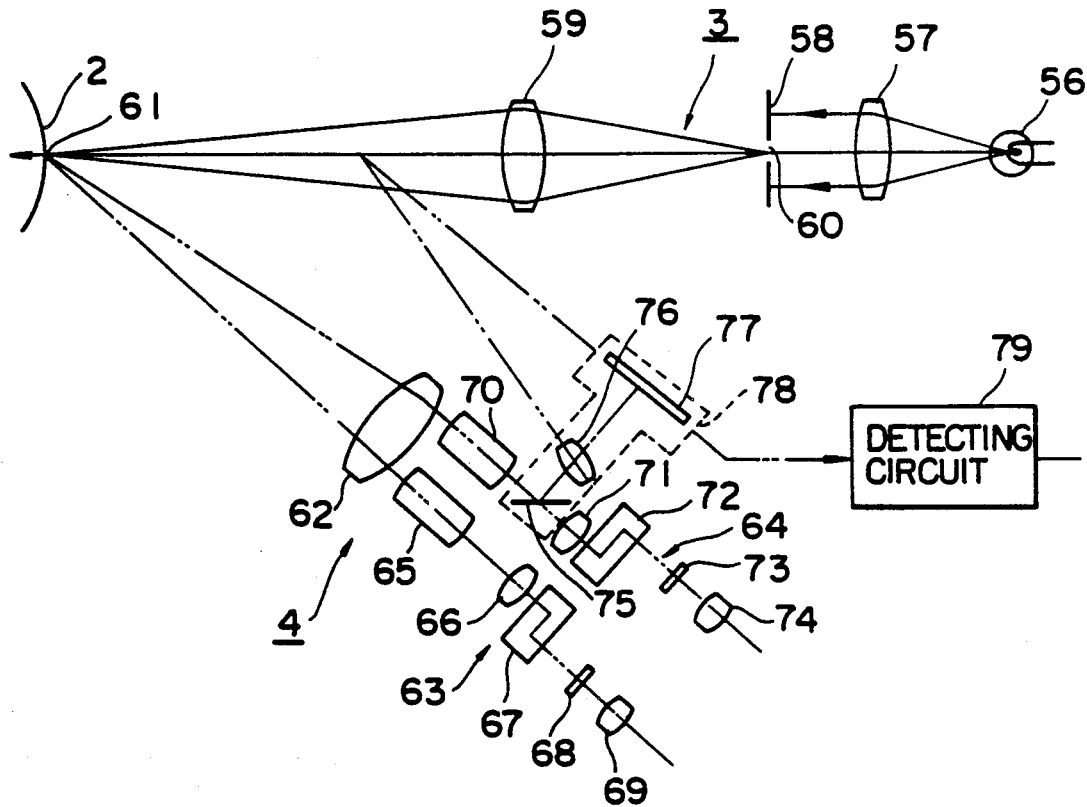
FIG. 7 is a schematic illustration of a third embodiment of the present invention.
Figure 8:
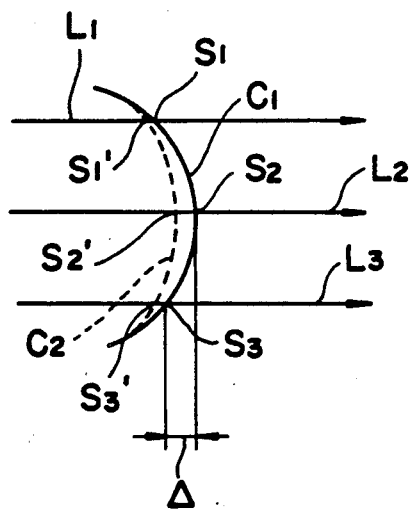
FIG. 8 is a schematic view for explaining the embodiment of FIG. 7.
Figure 9:
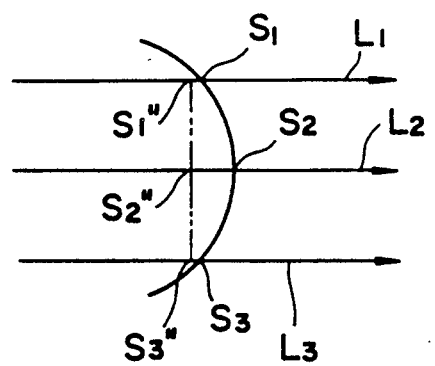
FIG. 9 is likewise a schematic view for explaining the embodiment of FIG. 7.

A third embodiment of the non-contact type tonometer according to the present invention will be described with reference to FIGS. 7 through 9. In this embodiment, the fluid discharge means 1 and the measuring circuit 24 are identical to those elements of the first embodiment, and the illustration thereof is accordingly eliminated.

A radiating optical system 3 generally comprises a light source 56, a condenser lens 57, a slit plate 58 and a projecting lens 59. An incandescent lamp is used as the light source 56.

The light source 56 is provided in the focal position of the condenser lens 57. The slit plate 58 is provided between the condenser lens 57 and the projecting lens 59 and includes an elongated slit 60. The detecting light permitted to pass through the slit 60 is projected as a slit projecting light 61 toward the cornea 2 by the projecting lens 59.

A detecting optical system 4 is constituted as an observation microscope. The detecting optical system 4 generally comprises an objective lens 62, a left eye optical system 63 and a right eye optical system 64. The left eye optical system 63 includes a variable power optical system 65, an image-formation lens 66, an erecting optical system 67, a focal plate 68 and an ocular 69. While, the right eye optical system 64 comprises a variable power optical system 70, an image-formation lens 71, an erecting optical system 72, a focal plate 73 and an ocular 74, and its slit shape in section can be observed by an operator.

The right eye optical system 64 is provided with a half mirror 75 between a variable power optical system 70 and an image-formation lens 71. The half mirror is disposed at an angle with respect to the optical axis of its right eye optical system 64. Since a part of the slit projecting light reflected on the cornea 2 is reflected on this half mirror 75, an image-formation lens 76 and an area sensor 77 are provided in the reflecting direction thereof. The image-formation lens 76 and the area sensor 77 are arranged in such a manner as to satisfy the Scheempflug's principle with respect to the slit projecting optical flux. Two dimensional type CCD are used for the area sensor 77, and the area sensor 77 has at least three scanning lines.

A conventional slit lamp can be used for the objective lens 62, left eye optical system 63 and right eye optical system 64. The half mirror 75, image-formation lens 76 and area sensor 77 may be stored in a case 78 for optional use. The sectional position of the cornea 2 can be controlled in its predetermined position by a measurer using the left eye optical system 63 as well as the right eye optical system 64. The slit projecting light reflected on the cornea 2 is formed with its image as a corneal sectional image on the area sensor 77 by the image-formation lens 76. FIG. 8 illustrates the corneal sectional image in which $C_1$ denotes a corneal sectional image before the cornea 2 is transfigured, $C_2$ denotes a corneal sectional image after the cornea 2 is transfigured by a quantity $\Delta$, and $L_1$, $L_2$, $L_3$ denote scanning lines. Since the component elements of the area sensor 77 are scanned by at least three scanning lines upon pressing a start button, an image-formation position can be obtained comprising the component elements forming the corneal sectional image.

In this embodiment, three image-formation positions $S_1$, $S_2$, $S_3$ are obtained and such obtained positional information is supplied to a detecting circuit 79 which has same the construction as the circuit 55 in the second aforementioned embodiment. A voltage corresponding to the address information of the element is supplied to the sample and hold circuit 38 of the measuring circuit 24 as an image-formation signal by the detecting circuit 79 prior to transfiguration. Since this scanning is made at a high speed, the image-formation position is varied from one minute to the next during the transfiguring process of the cornea 2. Accordingly, the image-formation position signals during the transfiguring process thereof are inputted in the detecting circuit 79 from one minute to the next, and the output voltage from the detecting circuit 79 is supplied to the sample and hold circuit 38. That is, the output voltage of the detecting circuit 79 is sampled as corneal transfiguration quantity data. In FIG. 8, $S'_1$, $S'_2$, $S'_3$ denote image-formation positions at a time when the cornea 2 is transfigured by a deformation quantity $\Delta$.

Applanation tonometry is known as one of the intraocular pressure measuring methods of the cornea 2 in which the cornea 2 is pressurized to form a circular plane with a diameter of 3.06 mm in order to eliminate the effects of the elastic force of the cornea and the adverse influence of the tear liquid to the intraocular pressure measurement. In case this applanation tonometry is used, the flow pressure of the fluid at a time when the image-formation positions $S''_1$ $S''_2$, $S''_3$ are in alignment with respect to each other, as shown in FIG. 9, can be used.

Figure 10:
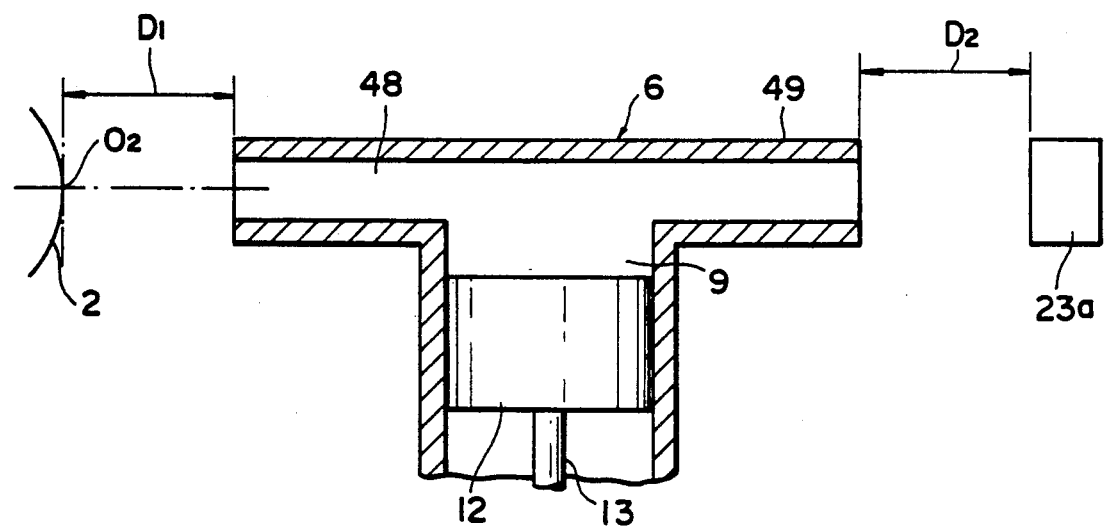
FIG. 10 is a partial sectional view of a fourth embodiment of the present invention.

A fourth embodiment of the non-contact type tonometer according to the present invention will be described with reference to FIG. 10. This embodiment describes a modified example of the second embodiment.

In this embodiment, the pressure sensor 23a is disposed in such a manner as that the distance $D_2$ between a tip portion of the nozzle 49 and the sensor 23a is equal to a distance $D_1$ between the tip portion of the nozzle 48 and the cornea when it is not transfigured. Thereby, the sensor 23a can detect the flow pressure of fluid under conditions equal to those under which the cornea receives the flow pressure of fluid.

The remaining construction of this embodiment is the same as the preceding embodiment, so that explanation will be eliminated.

Figure 11:
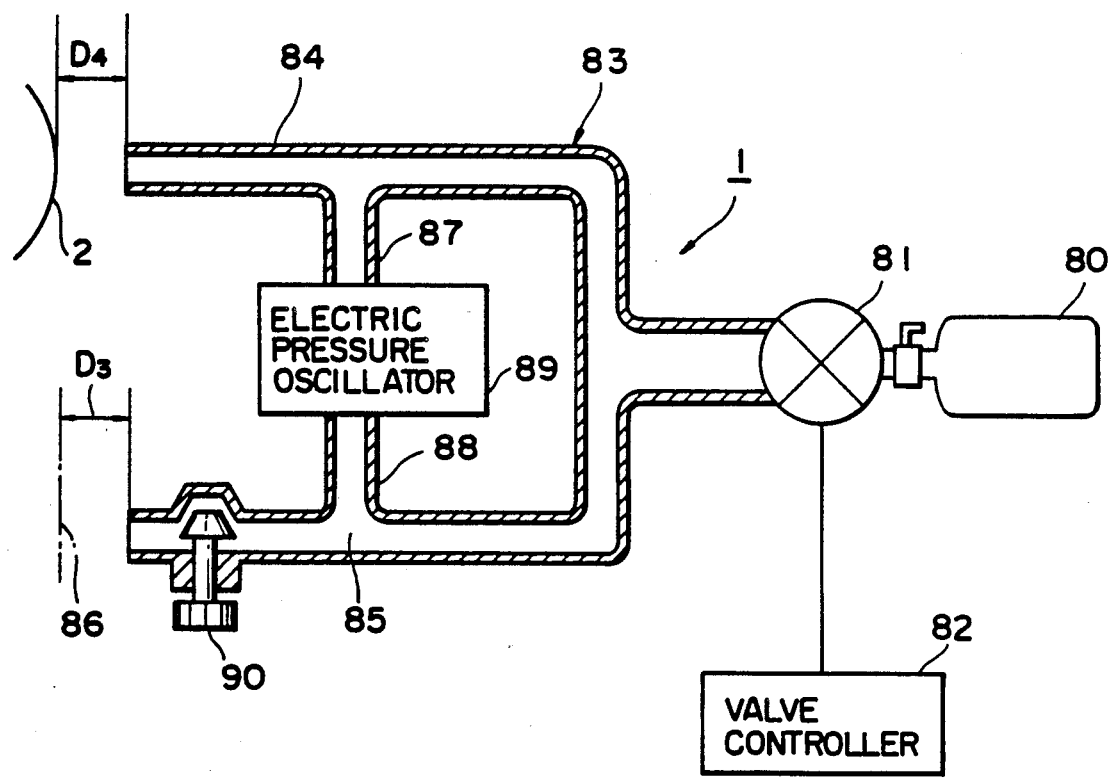
FIG. 11 is a partial sectional view of a fifth embodiment of the present invention.

FIG. 11 describes a fifth embodiment of the non-contact type tonometer according to the present invention.

In this embodiment, fluid discharging means 1 is composed with an air bomb 80, a valve 81, a valve controller 82 and a discharge tube 83. The valve controller 82 has a function to adjust the opening of the valve 81. The discharge tube 83 includes two tube portions 84, 85 extending in parallel to each other. The tube portion 84 extends toward the cornea 2 and the tube portion 85 extends toward a standard plate 86. The distance $D_3$ from a tip of the tube 85 to the standard plate 86 is equal to distance $D_4$ from a tip of the tube 84 to the vertex $O_2$ of the cornea 2.

The tube portions 84, 85 are provided with branch tubes 87, 88, respectively. Each branch tube 87, 88 is connected to an electric pressure oscillator 89. The electric pressure oscillator 89 outputs a signal based on differential pressure generated between the branch tubes 87 and 88 and operates as the pressure sensor 23a. The tube portion 85 is provided with an adjusting valve 90. This adjusting valve 90 adjusts the output of the electric pressure oscillator 89 to be zero when the cornea 2 is not transfigured.

Operation of this fifth embodiment will be described as follows. When the valve 81 is opened, air from the air bomb 80 flows toward the discharge tube 83 and is introduced along the tubes 84, 85 as pressurized fluid for transfiguring the cornea 2 under examination.

At a time before the cornea 2 is transfigured, there is no change in the relation between the discharging state of the tube portion 84 and a discharging state of the tube portion 85. Under these conditions the output of the electric pressure oscillator 89 is set to zero by adjustment of the adjusting valve 90.

When the valve 81 is further opened, the cornea 2 is transfigured by the flow pressure of the fluid, and there exists a change in the relation between the discharging state of the tube portion 84 and the discharging state of the tube portion 85. Accordingly, upon transfiguration of the cornea 2, pressure in the branch tube 87 begins to decrease according to the cornea transfiguration. On the other side, the standard plate 86 maintains its condition. Thereby, the pressure in the branch tube 88 remains constant. The electric pressure oscillator 89 changes from the equilibrium state and its output changes from zero. The output of the electric pressure oscillator is supplied to the sample and hold circuit 31 and the corresponding pressure data is sampled by the circuit 31.

The non-contact type tonometers as disclosed in the first through fifth embodiments are of a type in which the intraocular pressure is measured based on the physical measurements establishing the changes in ocular transfiguration corresponding to changes in the flow pressure. These embodiments have measured the changes in the quantity of the corneal reflection light or of the image-formation position of the corneal reflection light on a detector. In another type, the intraocular pressure is measured by measuring the changes in flow pressure corresponding to changes in the quantity of the reflection light from the cornea.

The present invention, however, is not limited to the above. In order to overcome the disadvantages which the related art has, the present invention is designed to accommodate changes in the temperature or density of the fluid, a secular change in the fluid discharging system, and also a change of the pressure of the discharged fluid due to incorrect operation. This is done by directly measuring the flow pressure of the fluid for corneal transfiguration.

Figure 12:
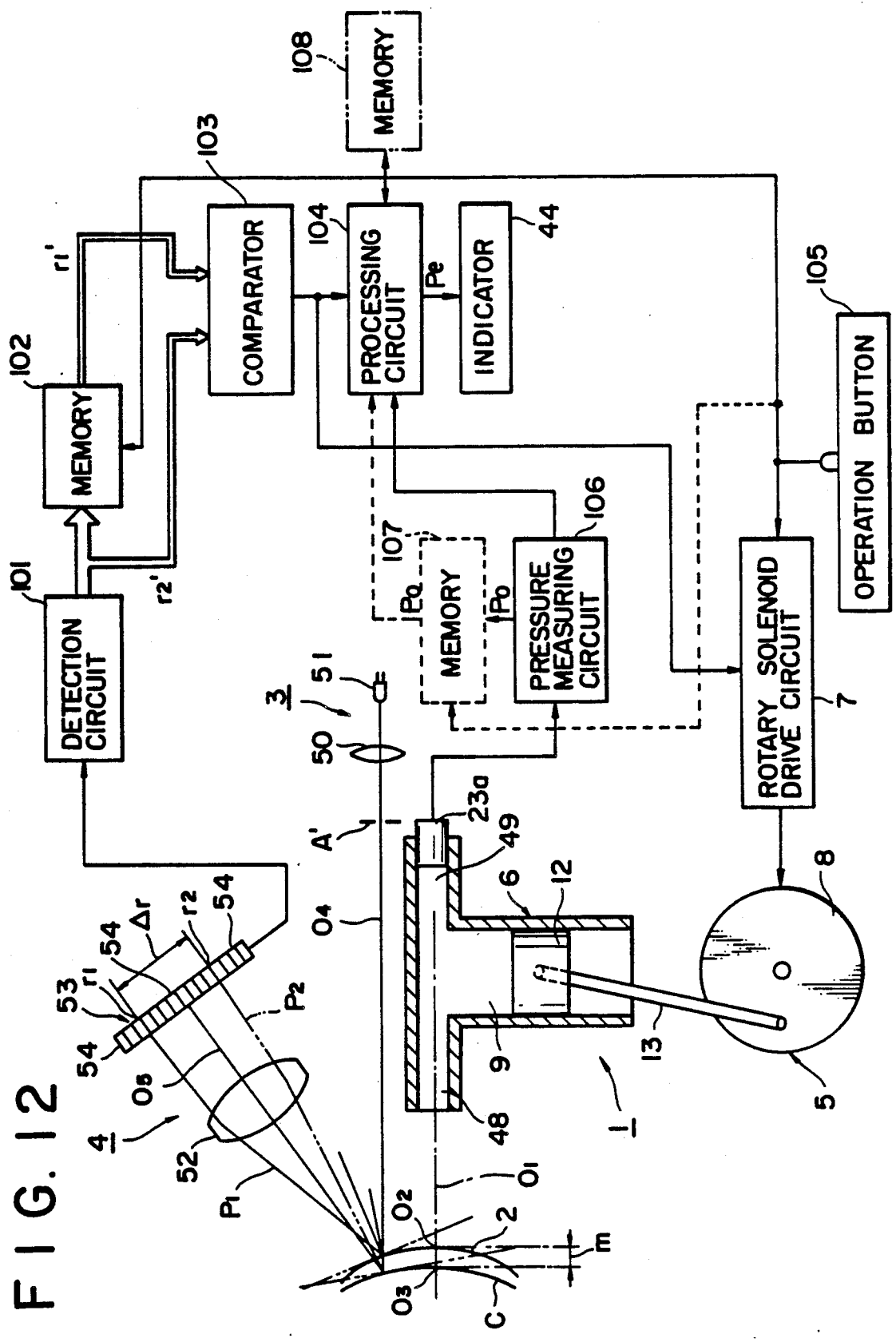
FIG. 12 is a schematic illustration of a sixth embodiment of a non-contact type tonometer according to the present invention.

FIG. 12 illustrates a sixth embodiment of the present invention. A corneal transfiguration detecting system shown in this figure is constructed in a manner similar to the above mentioned second embodiment (FIG. 6). Therefore, the elements of this embodiment are designated by the same reference numerals as those used in the second embodiment in order to avoid duplicate description.

A time series signal from a sensor 53 is inputted into a detection circuit 101. The detection circuit 101 outputs an address information to a memory circuit 102 and a comparator 103.

When the cornea 2 is tranfigured by a predetermined quantity m, the image formation position of the detection light is changed by $\Delta r$. The change $\Delta r$ of this image formation position correlates with the transfiguration quantity m. The change $\Delta r$ of this image-formation position is employed as a difference in the address information.

The memory circuit 102 is inputted with the address information corresponding to the image-formation position of the detection light before the cornea is transfigured from the detection circuit 101, and an address information r1' is memorized. The comparator 103 is then inputted with an address information r2' corresponding to the image-formation position of the detection light reflected on the cornea 2 as it is being transfigured and also with the address information r1' outputted from the memory circuit 102. The comparator 103 compares whether the difference between the address information r1' and the address information r2' is a predetermined address difference corresponding to the predetermined transfiguration quantity m, and outputs a corneal transfiguration detected signal to a processing circuit 104 and the rotary solenoid drive circuit 7 when the difference between the address information r1' and the address information r2' becomes the predetermined address difference corresponding to the predetermined transfiguration quantity m.

The solenoid drive circuit 7 is turned on by an operation button 105 and turned off by the output of the comparator 103. The memory circuit 102 is cleared before the solenoid drive circuit 7 as a consequence of activation of the operation button 105. The pressure sensor 23a outputs a detection signal to a pressure measuring circuit 106. The pressure measuring circuit 106 and the pressure sensor 23a are adapted to function as a flow pressure detecting means for detecting the flow pressure of the fluid which is generated in the hollow cylindrical portion 9.

The processing circuit 104 is turned on based on the output of the corneal transfiguration detected signal of the comparator 103, inputs a corresponding pressure Pa corresponding to the predetermined transfiguration quantity m, converts Pa to an intraocular pressure Pe and outputs the intraocular pressure converted signal Pe to the indicator 44.

In this embodiment, the memory circuit 107 is inputted with an initial pressure value Po before the intraocular pressure is measured. A pressure difference Pa' = -Pa−Po between a corresponding pressure Pa and the initial pressure value Po is determined by the processing circuit 104. This pressure difference Pa' is converted to the intraocular pressure Pe with a result that errors due to irregularity and drift of the character of the pressure sensor 23a and the pressure measuring circuit 106 are eliminated.

The intraocular pressure value can also be obtained in the following manner. The memory circuit 108 is loaded with the corresponding values of fluid pressure and intraocular pressure. The processing circuit 104 reads out the intraocular pressure Pe corresponding to the corresponding pressure Pa.

Figure 13:
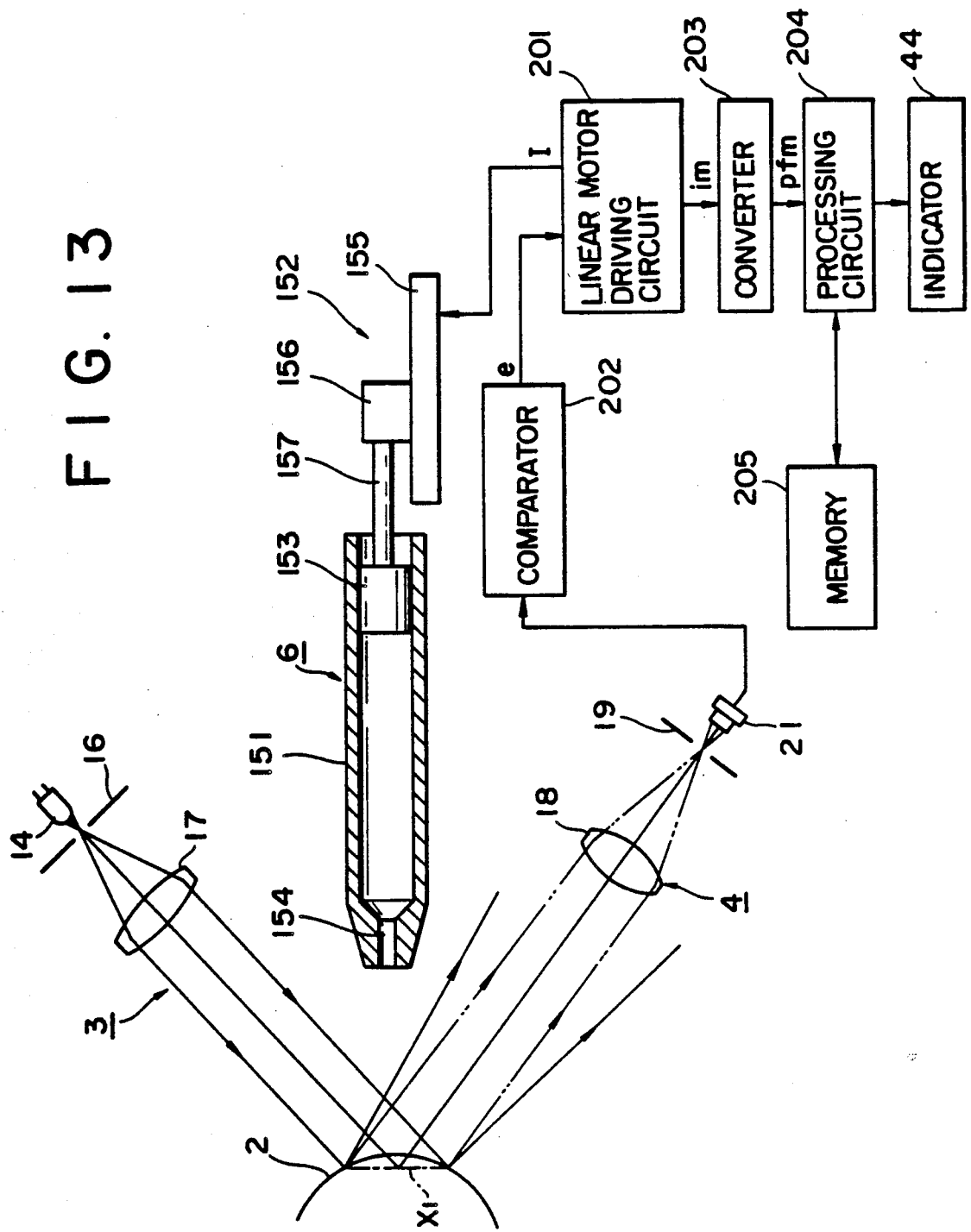
FIG. 13 is a schematic illustration of a seventh embodiment of a non-contact type tonometer according to the present invention.

A seventh embodiment of the present invention will be described with reference to FIG. 13. The non-contact type tonometer of this embodiment uses the correlation between the internal pressure of the cylinder at the time when the cornea 2 is pressurized to be in the applanation state and the driving force of the piston at the time when the piston is driven. In this embodiment, the internal pressure of the cylinder becomes the corresponding fluid pressure. Since the radiation optical system 3 and the detection optical system 4 are constituted in the same manner as those of the first embodiment, the corresponding elements are designated by identical reference numerals in order to avoid a duplicate description.

A fluid generating means 6 generally comprises a cylinder casing 151, a linear motor 152, and a piston 153. The cylinder casing 151 is formed at its tip end with a nozzle hole 154. The linear motor 152 generally comprises a reaction rail 155 and a moving element 156. The piston 153 is connected to the moving element 156 through a piston rod 157. The moving element 156 reciprocally driven on the reaction rail 155 to cause the piston 153 to be reciprocally moved within the cylinder casing 151. The reciprocal movement of the piston 153 causes a fluid to be discharged from the nozzle hole 154 toward the cornea 2.

The linear motor 152 is driven by a linear motor driving circuit 201. The output of the light receiving element 21 is inputted in a comparator 202. This comparator 202 determines whether or not the the output of the light receiving element 21 has reached a maximum.

The comparator 202 is designed to output a detection signal e to the linear motor driving circuit 201 at the time when the output of the light receiving element 21 becomes maximum. A current I for driving the linear motor 152 is gradually increased in order to increase the driving force of the piston 153. When this current I is increased, the internal pressure Pf within the cylinder is gradually increased. When the detection signal e is inputted, the linear motor driving circuit 201 outputs the current im flowing in the linear motor 152 at that time to a converter 203. The converter 203 converts the current im to a signal indicating the internal pressure Pfm of the cylinder. The output of the converter 203 is inputted to a processing circuit. The processing circuit 204 accesses a specific location in a memory circuit 205 based on the value internal pressure Pfm, reads out an intraocular pressure value stored at the specific location in the memory circuit 205, and outputs a signal indicating the intraocular pressure value to the indicator 44. In this embodiment, the converter 203, the linear motor driving circuit 201, and the comparator 202 serve as a pressure detecting means for detecting the intraocular pressure corresponding to the flow pressure of the fluid.

Although the present invention has been described with reference to the preferred embodiments, it is susceptible of further modifications and alternations without departing from the spirit and scope of the present invention.

What is claimed is:

1. A non-contact type tonometer comprising:
   means for discharging a gas under pressure toward a cornea of an eye to be tested in order to transfigure the cornea, said discharging means comprising a cylinder for storing the gas, a nozzle extending toward the cornea of the eye to be tested, a piston provided within said cylinder, and driving means for reciprocally moving said piston to discharge the gas from said nozzle toward the cornea;
   means for detecting the degree of physical transfiguration of the cornea caused by said discharge of said gas under pressure;
   means for measuring an intraocular pressure of the eye based on a pressure of said gas when the cornea is transfigured to a predetermined degree of physical transfiguration;
   said gas discharging means further including means for intentionally decreasing the pressure of said discharging means in accordance with a control signal generated in response to said transfiguration detecting means detecting that the cornea has been deformed to substantially said predetermined degree of physical transfiguration, said decreasing means including valve means communicating with said cylinder for exhausting gas from said cylinder when said valve means is opened to thereby decrease the gas pressure in said cylinder.

2. A non-contact type tonometer comprising:
   means for discharging a gas under pressure toward a cornea of an eye to be tested in order to transfigure the cornea, said discharging means comprising a cylinder for storing the gas, a nozzle extending toward the cornea of the eye to be tested, a piston provided within said cylinder, and driving means for reciprocally moving said piston to discharge the gas from said nozzle toward the cornea;
   means for detecting the degree of physical transfiguration of the cornea caused by said discharge of said gas under pressure;
   means for measuring an intraocular pressure of the eye based on a pressure of said gas when the cornea is transfigured to a predetermined degree of physical transfiguration;
   said gas discharging means further including means for intentionally decreasing the pressure of said discharging means in accordance with a control signal generated in response to said transfiguration detecting means detecting that the cornea has been deformed to substantially said predetermined degree of physical transfiguration; and
   said pressure decreasing means including means for controlling said driving means to cause withdrawal of said piston immediately before said transfiguration detecting means detects said predetermined degree of physical transfiguration.

3. A non-contact type tonometer according to claim 2, wherein said control means includes means for comparing a detected degree of physical transfiguration of the cornea detected by said cornea transfiguration detecting means with a standard value corresponding to said predetermined degree of physical transfiguration of the cornea, and for generating said control signal immediately before said detected degree of physical transfiguration matches said standard value.

4. A non-contact type tonometer according to claim 3, wherein said cornea transfiguration detecting means includes radiating optical means for projecting light flux toward the cornea, and detecting optical means for detecting a quantity of the light flux which is reflected by the cornea and which corresponds to said detected degree of physical transfiguration of the cornea.

5. A non-contact type tonometer according to claim 2, wherein said intraocular pressure measuring means includes a pressure sensor for detecting the pressure of said gas, and means for converting said detected pressure of said gas to an intraocular pressure of the eye to be tested.

6. A non-contact type tonometer according to claim 2, wherein said predetermined degree of physical transfiguration corresponds to applanation of the cornea.

7. A non-contact type tonometer according to claim 2, wherein said gas is air.

8. A non-contact type tonometer comprising:
   means for discharging a gas under pressure toward a cornea of an eye to be tested in order to transfigure the cornea, said discharging means comprising a cylinder for storing the gas, a first nozzle extending toward the cornea of the eye to be tested, a piston disposed within said cylinder, and driving means for reciprocally moving said piston to discharge the gas from said first nozzle toward the cornea in order to transfigure the cornea;
   means for detecting the degree of physical transfiguration of the cornea caused by said discharge of said gas under pressure;
   means for measuring an intraocular pressure of the eye based on a pressure of said gas when the cornea is transfigured to a predetermined degree of physical transfiguration;

said gas discharging means further including means for intentionally decreasing the pressure of said discharging means in accordance with a control signal generated in response to said transfiguration detecting means detecting that the cornea has been deformed to substantially said predetermined degree of physical transfiguration;

wherein said pressure decreasing means includes a second nozzle, connected to said cylinder, having an electromagnetic driving valve, driving means for opening said valve to exhaust said gas through said second nozzle, and control means for generating said control signal immediately before said transfiguration detecting means detects said predetermined degree of physical transfiguration of the cornea.

9. A non-contact type tonometer according to claim 8, wherein said control means includes means for comparing a detected degree of physical transfiguration of the cornea detected by said cornea transfiguration detecting means with a standard value corresponding to said predetermined degree of physical transfiguration of the cornea, and for generating said control signal immediately before said detected degree of physical transfiguration matches said standard valve.

10. A non-contact type tonometer according to claim 9, wherein said cornea transfiguration detecting means includes radiating optical means for projecting light flux toward the cornea, and detecting optical means for detecting a quantity of the light flux which is reflected by the cornea and which correspond to said detected degree of physical transfiguration of the cornea.

11. A non-contact type tonometer according to claim 8, wherein said intraocular pressure measuring means includes a pressure sensor for detecting the pressure of said gas, and means for converting said detecting pressure of said gas to an intraocular pressure of the eye being tested.

12. A non-contact type tonometer according to claim 8, wherein said predetermined degree of physical transfiguration corresponds to applanation of the cornea.

13. A non-contact type tonometer according to claim 8, wherein said gas is air.

14. A non-contact type tonometer comprising:

means for discharging a gas under pressure toward a cornea of an eye to be tested in order to transfigure the cornea, said gas discharging means comprising a cylinder for storing the gas, a nozzle extending toward the cornea of the eye to be tested, a piston provided within said cylinder, and driving means for reciprocally moving said piston to discharge the gas from said nozzle toward the cornea;

means for detecting the degree of physical transfiguration of the cornea caused by said discharge of said gas under pressure;

means for measuring the pressure of the gas in said cylinder and means for determining an intraocular pressure of the eye based on the measured pressure of said gas when the cornea is transfigured to a predetermined degree of physical transfiguration;

said gas discharging means further including means for intentionally decreasing the gas pressure in the cylinder in accordance with a control signal generated in response to said transfiguration detecting means detecting that the cornea has been deformed to substantially said predetermined degree of physical transfiguration;

said pressure decreasing means including means for controlling said driving means to cause withdrawal of said piston when the cornea is deformed to said predetermined degree of physical transfiguration.

* * * * *

UNITED STATES PATENT AND TRADEMARK OFFICE
CERTIFICATE OF CORRECTION

PATENT NO. : 5,002,056

DATED : March 26, 1991

INVENTOR(S) : Susumu Takahashi, Fumio Ohtomo

It is certified that error appears in the above-identified patent and that said Letters Patent is hereby corrected as shown below:

ON TITLE PAGE:
Assignee: Change "Tokyo Kabushiki Kikai Kabushiki Kaisha" to --Kabushiki Kaisha TOPCON--.

Signed and Sealed this

First Day of September, 1992

Attest:

DOUGLAS B. COMER

*Attesting Officer*    Acting Commissioner of Patents and Trademarks